United States Patent [19]

Mori et al.

[11] Patent Number: 5,707,833
[45] Date of Patent: Jan. 13, 1998

[54] PROCESS OF MAKING CYCLODEXTRIN GLUCANOTRANSFERASE WITH BREVIBACTERIUM

[75] Inventors: Shigeharu Mori; Tamio Mase; Takaichi Ohya, all of Aichi, Japan

[73] Assignee: Amano Pharmaceutical Co., Ltd., Nagoya, Japan

[21] Appl. No.: 471,235

[22] Filed: Jun. 6, 1995

Related U.S. Application Data

[63] Continuation of Ser. No. 194,220, Feb. 9, 1994, abandoned.

[30] Foreign Application Priority Data

Feb. 9, 1993 [JP] Japan ................................. 5-045747

[51] Int. Cl.$^6$ .................................................. C12P 21/04
[52] U.S. Cl. ......................... 435/71.2; 435/200; 435/169; 435/840
[58] Field of Search ..................... 435/71.2, 200, 435/169, 840

[56] References Cited

FOREIGN PATENT DOCUMENTS 0291067  11/1988  European Pat. Off. .

OTHER PUBLICATIONS

Bender, H, Arch Microbiol, vol. 110, pp. 271–282, 1977.
Goodfellow et al., "Biology of the Actinomycetes", 1984, Academic Press, pp. 44–46, 77–79.
Database WPI, Week 8107, Derwent Publications Ltd., AN 81–10404D, Dec. 1980.
Database WPI, Week 8710, Derwent Publications Ltd., AN 87–070684, Feb. 1987.
Database WPI, Week 8703, Derwent Publications Ltd., AN 87–017596, Dec. 1986.
Fujita et al., Purification and Properties of Cyclodextrin Glycosyltransferase from Bacillus sp. AL–6, Journal of Fermentation and Bioengineering, vol. 70, No. 3, pp. 150–154, 1990.
Tomita et al., Some Factors Affecting the Formation of γ–Cyclodextrin Using Cyclodextrin –Glycosyltransferase from Bacillus sp. AL–6, Journal of Fermentation and Bioengineering, vol. 70, No. 3, pp. 190–192, 1990.
Kato and Horikoshi, A New γ–Cyclodextrin Forming Enzyme Produced by Bacillus subtilis No. 313, J. Jpn. Soc. Starch Sci., 33, pp. 137–143, 1986. Abstract only.
Schmid et al., New Trends in Cyclodextrins and Derivatives, pp. 25–54, 1991.

Primary Examiner—Irene Marx
Attorney, Agent, or Firm—Sughrue, Mion, Zinn, Macpeak & Seas, PLLC

[57] ABSTRACT

This invention relates to a γ-cyclodextrin glucanotransferase having novel properties, to a process for the production of the γ-cyclodextrin glucanotransferase which comprises culturing a strain belonging to the genus Brevibacterium capable of producing cyclodextrin glucanotransferase, thereby allowing the strain to produce the γ-cyclodextrin glucanotransferase in a culture medium, and subsequently collecting the enzyme, to a process for the production of cyclodextrin which comprises allowing the cyclodextrin glucanotransferase to react with substrate dissolved in a solution, thereby effecting formation of γ-cyclodextrin as a main product, and to a method for increasing γ-cyclodextrin yield without accompanying yield increase of total cyclodextrin, which comprises adding ethyl alcohol to a reaction solution in which γ-cyclodextrin and β-cyclodextrin are formed from starch by the action of γ-cyclodextrin glucanotransferase, thereby effecting repressed formation of β-cyclodextrin and enhanced formation of γ-cyclodextrin. Development of the process of this invention has rendered possible low cost production of γ-cyclodextrin and therefore expands practical use of γ-cyclodextrin to the field of food and the like.

1 Claim, 3 Drawing Sheets

PROCESS OF MAKING CYCLODEXTRIN GLUCANOTRANSFERASE WITH BREVIBACTERIUM

This is a continuation of application Ser. No. 08/194,220 filed Feb. 9, 1994, now abandoned.

FIELD OF THE INVENTION

This invention relates to a substantially pure novel cyclodextrin glucanotransferase (EC 2.4.1.19, to be referred to as "CGTase" hereinafter), a process for the production of the novel enzyme and a process for the production of cyclodextrin (to be referred to as "CD" hereinafter) using the novel enzyme. More particularly, it relates to a process for the production of the novel CGTase which comprises culturing a strain belonging to the genus Brevibacterium capable of producing CGTase, thereby allowing the strain to produce the novel CGTase in a culture medium, and subsequently collecting the enzyme, to a process for the production of CD which comprises allowing the CGTase to react with a substrate in a solution, thereby effecting formation of γ-cyclodextrin (to be referred to as "γ-CD" hereinafter) as the main product, and to a method for increasing γ-CD yield without accompanying yield increase of total cyclodextrin (to be referred to as "T-CD" hereinafter) which comprises adding ethyl alcohol to a reaction solution in which γ-CD and β-cyclodextrin (to be referred to as "β-CD" hereinafter) are formed by the action of CGTase, thereby repressing formation of β-CD and enhancing formation of γ-CD.

BACKGROUND OF THE INVENTION

CD is a non-reducing circular maltooligosaccharide which is formed from glucose molecules by α-1,4-glucoside bonding. Since CD can form an inclusion compound by incorporating various guest molecules into the cavity of the circle of host molecules and change physical and chemical properties of the incorporated guest molecules, use of CD renders possible stabilization of compounds which are sensitive to oxidation or optical decomposition, fixation of volatile compounds, solubilization of hardly soluble compounds and deodorization of odor substances. Because of such capabilities, CD is used broadly in the field of pharmaceutical preparations, cosmetics, agricultural chemicals and food.

It is well known that typical CD includes α-CD consisting of 6 glucose molecules, β-CD consisting of 7 glucose molecules and γ-CD consisting of 8 glucose molecules, of which γ-CD is considered most useful in the field of pharmaceutical preparations, cosmetics, agricultural chemicals, food industries and the like due to its high solubility and excellent capability to form inclusion compounds.

Most of the CGTases known to date are those which produce α-CD and β-CD, and a CGTase capable of producing only γ-CD or γ-CD as a main product (γ-cyclodextrin glucanotransferase; to be referred to as "γ-CGTase" hereinafter) is known only in a few strains belonging to the genus Bacillus, namely a CGTase produced by Bacillus sp. AL6 (*J. Ferment. Bioeng.*, 70, 150–154 (1990) and *J. Ferment. Bioeng.*, 70, 190–192 (1990), reference 1), a CGTase produced by Bacillus sp. No. 313 (*J. Jpn. Soc. Starch Sci.*, 33, 137–143 (1986), reference 2) and a CGTase produced by *Bacillus firmus* 290–3 (*New Trend in Cyclodextrins and Derivatives*, p. 25 (1991), Editions de Sante (Paris, France); reference 3). (The term "JP-A" as used herein means an "unexamined published Japanese patent application".)

In consequence, α-CD and β-CD have been used in various fields, but almost no practical use exists in the case of γ-CD.

SUMMARY OF THE INVENTION

In view of the above, it therefore becomes an object of the present invention to obtain a novel γ-CGTase by isolating a microorganism capable of producing a novel γ-CGTase which produces γ-CD, culturing the microorganism to allow it to produce the γ-CGTase in a culture medium and then collecting the enzyme, and to provide an industrial process for the production of γ-CD using the novel enzyme.

Another object of the present invention is to solve the problem that the γ-CD content in a reaction system decreases and the β-CD content increases when concentration of starch as the substrate is increased or the enzyme reaction time is prolonged for the purpose of providing γ-CD at a low cost using the novel γ-CGTase of the present invention.

Other objects and advantages of the present invention will be made apparent as the description progresses.

DETAILED DESCRIPTION OF THE INVENTION

Figure 1:
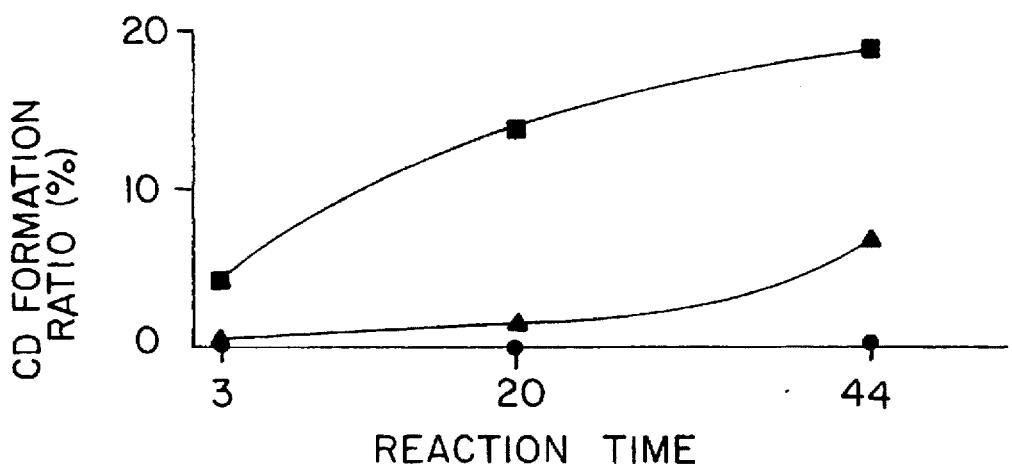
FIG. 1 is a graph showing a relationship between the reaction time and the amount of cyclodextrins formed when the γ-CGTase of the present invention is allowed to react with starch.

The inventors of the present invention have examined a broad range of natural sources to screen microorganisms capable of producing a novel γ-CGTase which can produce γ-CD and found a strain belonging to the genus Brevibacterium which can produce the intended γ-CGTase. Thereafter, the present inventors succeeded in culturing the strain with the production of the γ-CGTase in the resulting culture, and collected the enzyme therefrom and confirmed novel properties of the enzyme. Further, the inventors established an industrial process for the production of γ-CD making use of this novel enzyme.

In addition, the present inventors have made an attempt to enhance production of γ-CD by adding ethyl alcohol to a reaction solution in which γ-CD and β-CD are produced from a high concentration of starch by the action of the γ-CGTase of the present invention, and found for the first time that the effect of the addition of ethyl alcohol was not only to simply enhance production of γ-CD but also to repress production of β-CD while enhancing production of γ-CD, namely found an effect of ethyl alcohol to enhance production of γ-CD without increasing yield of T-CD.

The present invention was accomplished based on these findings.

Though a method for increasing yield of α-CD has been reported in which ethyl alcohol is added to a reaction solution containing an α-CGTase (JP-B-60-25118; the term "JP-B" as used herein means an "examined Japanese patent publication"), this is a method to increase the yield of α-CD without repressing simultaneous forming of β-CD and γ-CD. Thus, yield increase of T-CD accompanies this method.

Also, a method for increasing yield of γ-CD has been reported in which ethyl alcohol is added to a reaction solution containing a γ-CGTase (JP-A-62-25976), but it discloses nothing about repression of the simultaneous formation of β-CD.

It is desirable to repress formation of β-CD to a level as low as possible, because its presence in other cyclodextrins (α-CD and γ-CD) spoils commercial values of CD syrup and the like, which is caused by the nature of β-CD to crystallize easily due to its extremely low solubility in water in comparison with other cyclodextrins.

In consequence, the present invention which provides a process in which yield of γ-CD is increased while repressing formation of β-CD is useful and novel.

As a result of extensive studies on the basis of the above findings, the present inventors have accomplished the present invention by establishing a method for increasing yield of γ-CD in which formation of γ-CD is enhanced without increasing yield of T-CD, namely with repression of β-CD formation.

Though any known γ-CGTase may be used for the method described above provided that it can form γ-CD and β-CD from starch by its enzyme reaction, it is preferable to use the γ-CGTase produced by the Brevibacterium species which has been isolated by the present inventors from a soil sample.

The following summarizes bacteriological properties of the strain newly found in and isolated from a soil sample by the present inventors.

(1) Morphological characteristics
Shape and size of cell: slender bacillary cell with swelling at the both ends of the cell, a size of 0.5–0.7×5.0–20 μm
Pleomorphism: recognizable
Motility: motile (peritrichous flagella)
Spore: no sporulation
Gram-staining: negative
Acid fastness: negative (2) Growth characteristics on the following media
Bouillon agar plate culture: slightly weak growth with smooth-surfaced viscous colonies (2 to 3 mm in diameter) having translucent periphery
Bouillon agar slant culture: slightly weak growth with straight, raw color and translucent surface
Bouillon broth culture: slight turbidness of whole liquid medium with viscous cell precipitate in the bottom
Litmus milk culture: no changes (3) Physiological characteristics
Behavior to oxygen: obligately aerobic
Catalase: positive
Oxidase: negative
OF test: no fermentation or oxidation
Production of gas from glucose: negative
Formation of indole: negative
Reduction of nitrate: positive
Hydrolysis of tyrosine: negative
Hydrolysis of starch: positive
Hydrolysis of casein: negative
Hydrolysis of gelatin: positive
Dihydroxyacetone: negative
Phenylalanine deaminase: negative
Egg yolk reaction: negative
Growth in 0.001% lysozyme: negative
Urease: negative
TSI agar medium (acid on slant): red/red
Formation of hydrogen sulfide: negative
Growth in MacConkey agar medium: negative
Growth in YMA medium: negative
Growth in bismuth bouillon: negative
Formation of 3-keto-lactic acid: negative
Growth in NaCl medium: positive at 0.5 to 15% (w/v) NaCl and negative at 20% (w/v) NaCl
Range of temperature for growth: 16° to 45° C. (optimum at 36° to 38° C.)
Range of pH for growth: 8.0 to 11.6 (optimum at 8.5 to 9.0)
Formation of acids from sugars:
L-arabinose
Xylose
Glucose
Mannitol
Salicin
Starch When taxonomic position of this strain was examined by evaluating these bacteriological properties with reference to Bergey's Manual of Systematic Bacteriology (Vol. 2, 1986), it did not belong to any of the genera Acinetobacter, Rhizobium, Agrobacterium, Natronobacterium and Bacillus, but to the coryneform type, because this strain was negative in Gram-staining and cytochrome oxidase test and it had peritrichous flagella, produced no spores and formed no acids from sugars. On the basis of these findings, this strain was identified as a species belonging to the genus Brevibacterium which is a member of the coryneform type.

Since the above bacteriological properties did not coincide with those of known Brevibacterium species or strains, the present inventors have judged this bacterium to be a new strain and named it Brevibacterium sp. No. 9605. This strain has been deposited by the present inventors since Sep. 2, 1992 with National Institute of Bioscience and Human-Technology, Agency of Industrial Science and Technology, MITI, 1–3, Higashi 1-chome, Tsukuba-shi, Ibaraki-ken 305, Japan and has been assigned the accession number FERM P-13141 (FERM BP-4537 under the Budapest Treaty).

Brevibacterium strains which can produce CGTase has not been reported to date, and this strain is the first Brevibacterium strain which can produce CGTase.

To produce γ-CGTase by making use of this strain, the microorganism is cultured in a synthetic or natural medium containing a carbon source, a nitrogen source, inorganic salts and other nutrients which are necessary for obtaining good growth of the strain and proper production of the enzyme. The carbon source may be selected from carbohydrates such as starches or compositional fractions (amylose, amylopectin, etc.) thereof, roasted dextrins, modified starches, starch derivatives, physically treated starches, α-starches and the like. Illustrative examples of the carbohydrates include soluble starch, corn starch, potato starch, sweet potato starch, dextrin, amylopectin, amylose and the like.

Examples of the nitrogen source include organic nitrogen sources such as peptone, casein, meat extract, yeast extract, corn steep liquor, soybean or a soybean cake and the like, inorganic salts of nitrogen compounds such as ammonium sulfate, ammonium phosphate and the like and amino acids such as glutamic acid and the like.

Examples of inorganic salts include phosphates such as potassium dihydrogenphosphate, dipotassium hydrogenphosphate and the like, magnesium salts such as magnesium sulfate and the like, calcium salts such as calcium chloride and the like and sodium salts such as sodium carbonate and the like.

It is desirable to carry out cultivation of the strain under an aerobic condition for example by shaking culture, agitation culture with aeration or the like at a medium pH of from 7 to 11, preferably from 8 to 10 and at a temperature of from 10° C. to 40° C., preferably from 25° C. to 37° C. However, these culture conditions are not particularly limited provided that other conditions can provide proper growth of the strain and production of the enzyme of interest.

When cultured under such conditions, γ-CGTase is produced in the culture medium generally 2 to 7 days after starting the culturing. Thereafter, cells are removed from the culture medium to obtain a culture filtrate, and the enzyme of interest is recovered from the filtrate by subjecting it to desalting and concentration using ultrafiltration membranes and then to ammonium sulfate salting out, organic solvent precipitation or the like. Though the thus obtained crude γ-CGTase as such can be used in the CD forming reaction, it may optionally be further purified by, for example, an absorption/elution technique using DEAE-Sephadex (a trademark, manufactured by Pharmacia) or Butyl-Toyopearl (a trade name, manufactured by Tosoh Corporation), by a fractionation technique using Sephadex (a trademark, manufactured by Pharmacia) or Toyopearl (a trade name, manufactured by Tosoh Corporation) or by an affinity chromatography using γ-CD-Sepharose.

The following describes enzymological properties of the γ-CGTase of the present invention.

(1) Action and substrate specificity: The enzyme of the present invention (5 units) was added to 2% by weight soluble starch aqueous solution (pH 7.0) and incubated at 40° C. to measure the time-course of amounts of CD formed during the reaction by a high performance liquid chromatography. The conditions for the HPLC is the same as those employed in Example 2 described below. The results are shown in FIG. 1 in which a black square indicates the ratio of formed γ-CD, a black triangle indicates the ratio of formed β-CD and a black circle indicates the ratio of formed α-CD. Each CD formation ratio is expressed as a weight percentage to the substrate starch. As is evident from the results shown in FIG. 1, this enzyme acts upon starch and forms mainly γ-CD, as well as β-CD, but does not form α-CD.

Figure 2:
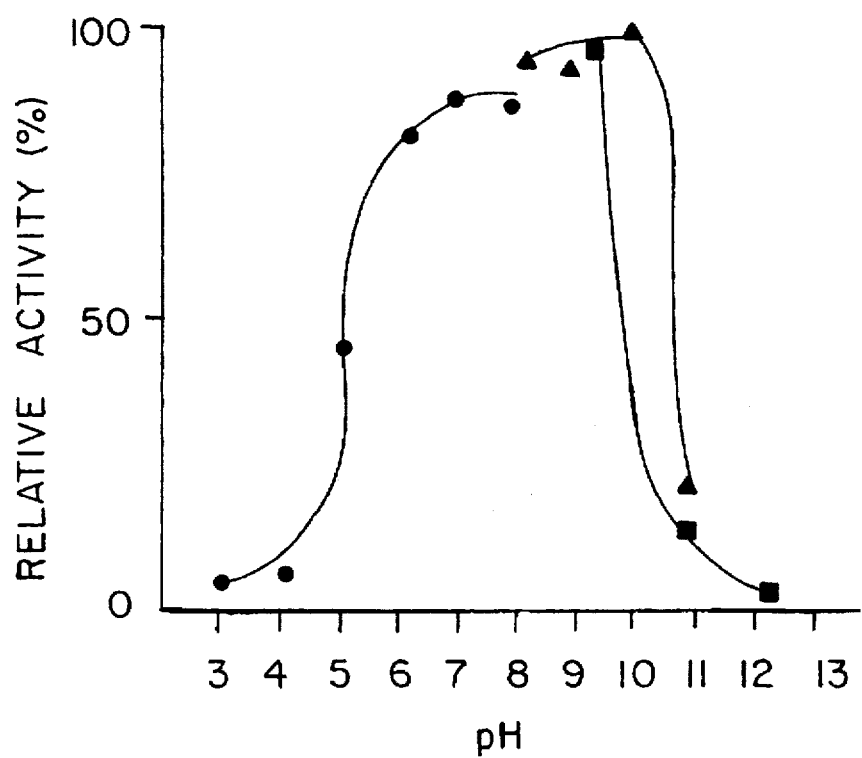
FIG. 2 is a graph showing an optimum pH profile of the γ-CGTase of the present invention. In the figure, a black circle indicates use of McIlvaine buffer, a black triangle indicates use of Atkins & Pantin buffer and a black square indicates use of KCl-NaOH buffer.

(2) Optimum pH: The enzyme of the present invention (1 unit/ml aqueous solution) was added to 1.5% by weight soluble starch aqueous solution and incubated for 30 minutes at 40° C. with varied pH conditions of from 3 to 13 to measure the enzyme activity under each condition. The results are shown in FIG. 2. As is evident from the results shown in FIG. 2, this enzyme has an optimum pH of about 8 to about 9.

Figure 3:
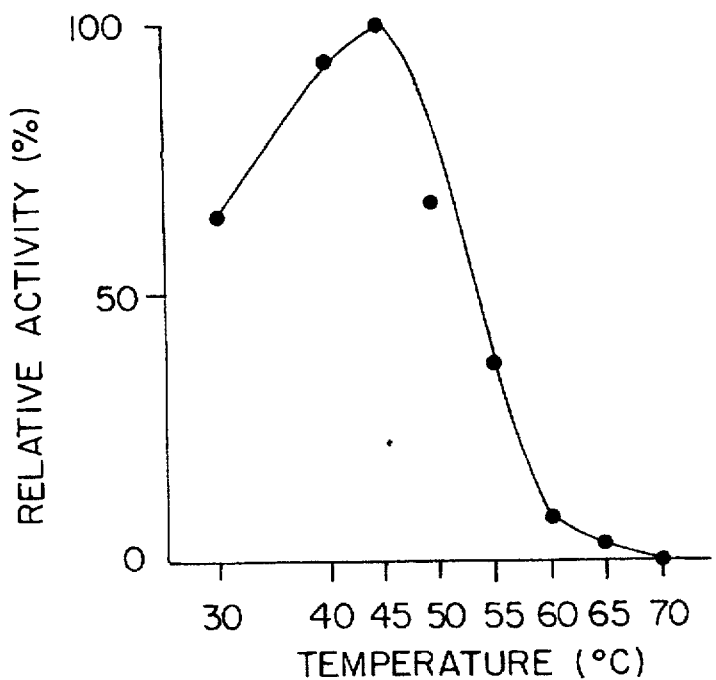
FIG. 3 is a graph showing an optimum temperature profile of the γ-CGTase of the present invention.

(3) Optimum temperature: The enzyme of the present invention (1 unit/ml aqueous solution) was added to 1.5% by weight soluble starch aqueous solution and incubated for 30 minutes at pH 10.0 with varied temperature conditions to measure the enzyme activity under each condition. The results are shown in FIG. 3. As is evident from the results shown in FIG. 3, this enzyme has an optimum temperature of around 45° C.

Figure 4:
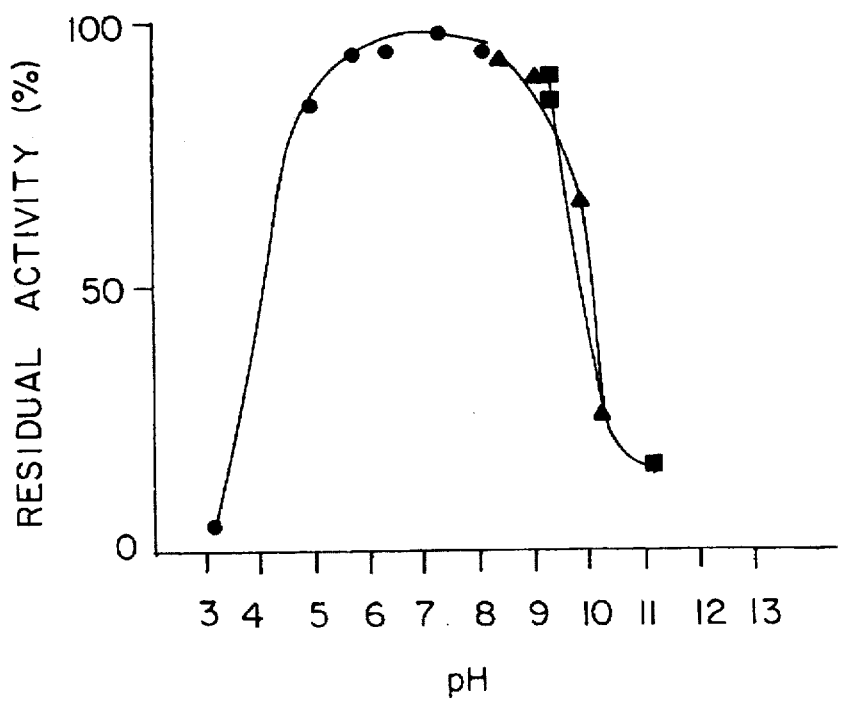
FIG. 4 is a graph showing a pH stability profile of the γ-CGTase of the present invention. In the figure, a black circle indicates use of McIlvaine buffer, a black triangle indicates use of Atkins & Pantin buffer and a black square indicates use of KCl-NaOH buffer.

(4) Stable pH range: A solution of the enzyme of the present invention (5 units/ml aqueous solution) was incubated for 30 minutes at 40° C. with varied pH conditions of from 3 to 13 to measure residual enzyme activity under each condition. The results are shown in FIG. 4. As is evident from the results shown in FIG. 4, this enzyme has a stable pH range of from about 6 to about 8.

Figure 5:
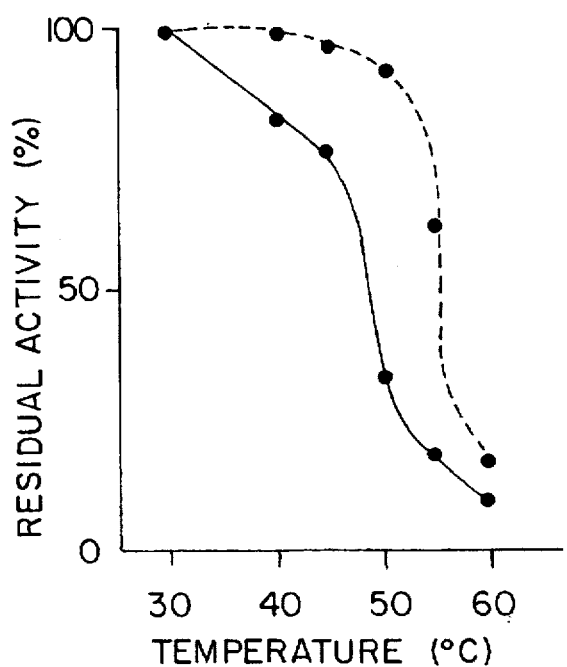
FIG. 5 is a graph showing a temperature stability profile of the γ-CGTase of the present invention. In the figure, a solid line indicates a result when the γ-CGTase was used alone and a dotted line indicates a result when 20 mM of calcium chloride was added.

(5) Temperature stability: An aqueous solution of the enzyme of the present invention was incubated for 30 minutes at pH 9.0 (0.1M $H_3BO_3$·KCl-NaOH buffer) with varied temperature conditions to measure residual enzyme activity under each condition. The results are shown as a solid line in FIG. 5. As is evident from the results shown in FIG. 5, this enzyme shows about 85% residual activity at 40° C. This enzyme is stabilized by the addition of a calcium salt and, as shown in FIG. 5 by a dotted line, it shows about 100% residual activity even after its treatment at 45° C. when 20 mM of calcium chloride is added.

(6) Effects of metal salts: The enzyme of the present invention was treated with 1 mM of each metal salt at 40° C. for 10 minutes in 0.1M $H_3BO_3$·KCl-NaOH aqueous buffer (pH 8.0) to measure its residual activity, with the results shown in Table 1. As is evident from the results shown in Table 1, the enzyme of the present invention was inhibited by nickel, copper, zinc and silver and inactivated almost completely by mercury and cadmium.

TABLE 1

| Metal Salt | Residual Activity (%) |
|---|---|
| Control | 100 |
| $MgCl_2$ | 102 |
| $MnCl_2$ | 112 |
| $CoCl_2$ | 98 |
| $CaCl_2$ | 101 |
| $SrCl_2$ | 116 |
| $NiCl_2$ | 72 |
| $BaCl_2$ | 107 |
| $FeCl_2$ | 112 |
| $CuCl_2$ | 14 |
| $ZnCl_2$ | 26 |
| $HgCl_2$ | 0 |
| $AgNO_3$ | 22 |
| $SnCl_2$ | 100 |
| $CdCl_2$ | 2 |
| $FeCl_3$ | 109 |

(7) Effects of inhibitors: The enzyme of the present invention was treated with 1 mM of each inhibitor at 40° C. for 10 minutes in 0.1M $H_3BO_3$·KCl-NaOH aqueous buffer (pH 8.0) to measure its residual activity, with the results shown in Table 2. As is evident from the results shown in Table 2, the enzyme of the present invention was hardly inhibited by any of the used inhibitors. In Table 2, EDTA means ethylenediaminetetraacetic acid, SDS means sodium dodecyl sulfate, PCMB means p-chloromercuribenzoic acid, MIA means monoiodoacetic acid and NEM means N-ethylmaleimide.

TABLE 2

| Inhibitors | Residual Activity (%) |
| --- | --- |
| Control | 100 |
| EDTA | 93 |
| SDS | 84 |
| PCMB | 83 |
| MIA | 82 |
| NEM | 84 |

(8) Activity measurement: In the measurements of the enzlanological properties described above, enzyme activity was measured by the following method. A 0.05 ml portion of an aqueous solution of the enzyme was added to 0.5 ml of a substrate solution (1.5% by weight soluble starch in 0.1M Atkins & Pantin buffer, pH 10.0) and incubated at 40° C. for 30 minutes. After adding 5 ml of 0.1N hydrochloric acid to terminate the reaction, a 0.5 ml portion of the reaction mixture was taken out and mixed with 5 ml of an iodine solution (0.005% iodine in 0.05% potassium iodide solution) to measure decrease in the absorbance at 660 um. One unit of the activity was defined as the amount of enzyme which decreases 1% of the absorbance at 660 nm within 1 minute under these conditions.

(9) Molecular weight: The enzyme of the present invention has a molecular weight of about 75,000 (by SDS-electrophoresis).

(10) Isoelectric point: The enzyme of the present invention has an isoelectric point (pI) of 2.8 (by isoelectric focusing).

Enzymological properties of the enzyme of the present invention are shown in Table 3 together with those of the prior art CGTases which form γ-CD as the main product.

TABLE 3

| | Enzyme of reference 1 (Bacillus sp. AL6) | Enzyme of reference 2 (Bacillus sp. No. 313) | Enzyme of reference 3 (Bacillus firmus 29) | Enzyme of this invention (Brevibacterium sp. No. 9605) |
| --- | --- | --- | --- | --- |
| Optimum pH | 7.0 | 8.0 | 6–8 | 8–9 |
| Optimum temp. | 60° C. | 65° C. | 50° C. | 45° C. |
| Stable pH | 6–10.7 | 6–8 | — | 6–8 |
| Stable temp. | 55° C. | 50° C. | — | 40° C. |
| Ca dependence | no | no | no | yes |
| Main product CD | γ-CD | γ-CD | γ-CD | γ-CD |
| By-product CD | β-CD | none | β-CD | β-CD |

*: stability in the presence of 10 mM calcium chloride

As is evident from the data shown in Table 3, the enzyme of the present invention is a novel enzyme which is different from all of the prior art CGTases which form γ-CD as the main product.

According to a preferred example of the CD producing process of the present invention, an enzyme itself or a solution of the enzyme of the present invention (purified or crude preparation) is added in an amount of from 0.5 to 20 units (per 1 g of dry starch) to an aqueous solution containing 1 to 30% by weight of starch (or a compositional fraction thereof, a modified starch or the like such as dextrin, amylopectin, amylose, glycogen, oligosaccharides, etc.), and the enzyme reaction is carried out at a pH value of from 4 to 10 and at a temperature of from 20° to 70° C. for a period of from 1 to 50 hours. If necessary, the starch material may be used after liquefying it with heat.

Thus, the present invention has rendered possible production of γ-CD in an industrial scale, but with a newly found problem that the γ-CD content in a reaction system decreases and the β-CD content increases when concentration of starch as the substrate is increased and the enzyme reaction time is prolonged for the purpose of providing γ-CD in a more larger amount.

In consequence, the inventors of the present invention have conducted extensive studies with the aim of producing γ-CD at a low cost and found that the above problem can be solved by employing a process in which ethyl alcohol is added to a reaction solution for use in the γ-CGTase reaction under a condition of high starch concentration or prolonged reaction period, thereby effecting enhanced formation of γ-CD while simultaneously repressing formation of β-CD.

In this case, it is desirable to use ethyl alcohol in an amount of from about 5 to 30% (v/v), preferably from about 15 to 25% (v/v), as the final concentration based on the substrate solution, independent of the type of enzyme and concentration of the substrate.

Though the addition of ethyl alcohol may be effected at any time during the course of the reaction with no particular limitation, it may be added preferably at an early stage of the reaction, for example simultaneously with the reaction.

Unless otherwise indicated, all parts, percentages, ratios and the like used hereinafter are by weight.

EXAMPLES

The following Test Examples and Examples are provided to further illustrate the present invention. It is to be understood, however, that they are for purpose of illustration only and the present invention is not be construed as being limited thereto.

EXAMPLE 1

Each of 500 ml capacity Shaking flask was charged with 100 ml of a culture medium (pH 10.0) consisting of 1.0% soluble starch, 0.5% polypeptone, 0.25% yeast extract, 0.1% ammonium sulfate, 0.05% $K_2HPO_4$, 0.025% $MgSO_4\cdot 7H_2O$, 0.01% $CaCl_2$ and 1.0% $Na_2CO_3$ (separate sterilization). The thus prepared medium was sterilized in the usual way (at about 121° C., 10 to 20 minutes) and then inoculated with cells of Brevibacterium sp. No. 9605 (FERMP-13141, FERM BP-4537 under the Budapest Treaty). After 40 hours of culturing on a shaker at 37° C., the cultured cells were removed by centrifugation to obtain two liters of culture filtrate. Thereafter, the thus prepared culture filtrate was passed through an ultrafiltration membrane (Module SIP, manufactured by Asahi Kasei Kogyo Kabushiki Kaisha) to obtain 30 ml of a concentrated solution which showed a CGTase activity of 6.7 units/ml.

TEST EXAMPLE 1

The solution of γ-CGTase obtained in Example 1 (1, 2.5, 5 or 10 units per 1 g dry starch) was added to 2% potato starch solution (0.01M McIlvaine buffer (pH 7.0)) to carry out 3 to 44 hours of reaction at 40° C. The results are shown in Table 4.

TABLE 4

| Enzyme | Reaction Time | CD Forming Ratio (%) | | | |
|---|---|---|---|---|---|
| (u/g · DS) | (hr) | α-CD | β-CD | γ-CD | T-CD |
| 1.0 | 44 | — | 5.4 | 17.6 | 22.9 |
| 2.5 | 20 | — | 6.3 | 18.1 | 24.4 |
| 5.0 | 20 | — | 10.9 | 16.2 | 27.1 |
| 10.0 | 3 | — | 4.5 | 17.2 | 21.7 |

In this table, u/g·DS means unit of enzyme per 1 g of dry starch, and the CD forming ratio is expressed by weight ratio (%) based on the substrate.

As is evident from the results shown in Table 4, the enzyme of the present invention can form γ-CD with a yield of 16 to 18%.

EXAMPLE 2

Figure 6:
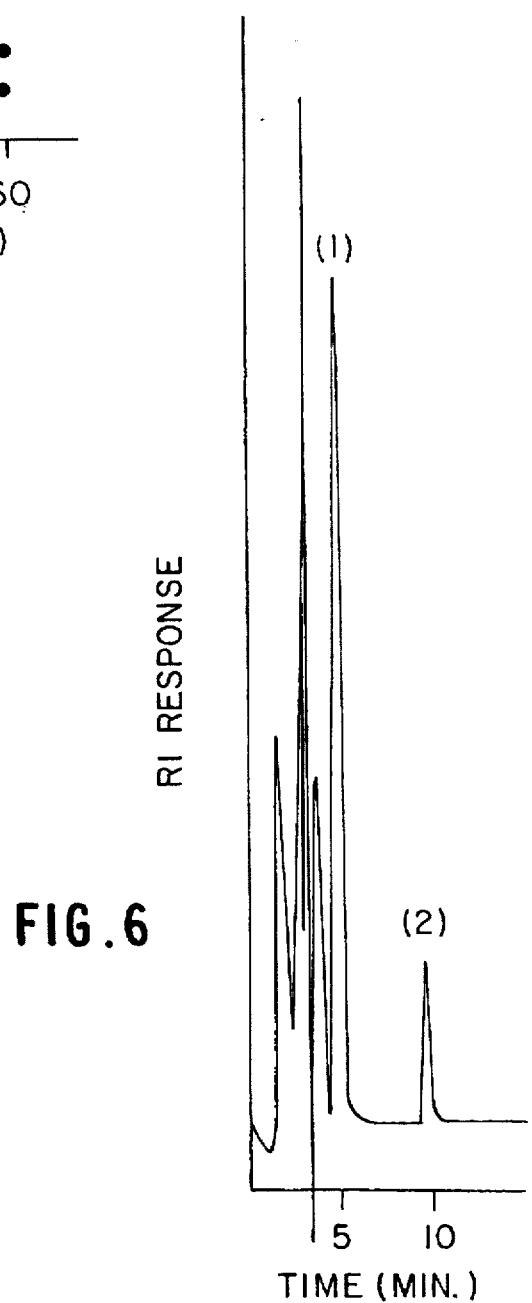
FIG. 6 is a chromatogram showing results of a high performance liquid chromatographic analysis of various cyclodextrins formed by the reaction of the γ-CGTase of the present invention with starch. In the figure, (1) indicates a peak of γ-CD and (2) indicates a peak of β-CD.

The solution of γ-CGTase obtained in Example 1 (2.5 units per 1 g of dry starch) was added to 10 ml of 2% potato starch solution (0.01M McIlvaine buffer, pH 7.0), and the enzyme reaction was carried out for 20 hours at 40° C. Yields of the γ-CD and γ-CD formed by this reaction (weight ratio to the substrate) were found to be 18.1% and 6.3%, respectively, with no formation of α-CD. Results of the analysis of the reaction solution by a high performance liquid chromatography are shown in FIG. 6.

Conditions for HPLC

Column: YMC-packed Column ODS-AQ303 (YMC Co.)
Temperature: 35° C.
Eluent: 12% methanol
Flow Rate: 1.0 ml/min.
Detection: Differential refractometryby the use of a refractometer Shimazu RID-6A (Shimazu Seisakusho)

EXAMPLE 3

The solution of γ-CGTase obtained in Example 1 (2.5 units per 1 g of dry starch) was added to 10 ml of 5% potato starch solution (0.01M $H_3BO_3$·KCl-NaOH aqueous buffer, pH 8.0), and the enzyme reaction was carried out for 44 hours at 55° C. Yields of the γ-CD and β-CD formed by this reaction (weight ratio to the substrate) were found to be 9.0% and 4.9%, respectively, with no formation of α-CD.

TEST EXAMPLE 2

The solution of γ-CGTase obtained in Example 1 (5 units per 1 g of dry starch) was added to 10 ml of 2 to 15% soluble starch solution (0.01M McIlvaine buffer, pH 7.0), and the enzyme reaction was carried out for 3 to 44 hours at 40° C. to examine formation ratio of each CD. Formation ratio of each CD by the Brevibacterium sp. γ-CGTase is shown in Table 5. In the table, each CD formation ratio is expressed as a weight ratio to the substrate.

TABLE 5

| Substrate | Reaction Time | CD Forming Ratio (%) | | | |
|---|---|---|---|---|---|
| (%) | (hr) | α-CD | β-CD | γ-CD | T-CD |
| 2.0 | 3 | — | 2.9 | 8.5 | 11.4 |
| 2.0 | 22 | — | 11.0 | 15.1 | 26.1 |
| 2.0 | 44 | — | 18.7 | 11.7 | 30.4 |
| 5.0 | 22 | — | 13.2 | 5.8 | 19.0 |
| 10.0 | 22 | — | 8.5 | 4.6 | 13.1 |
| 15.0 | 22 | — | 7.8 | 3.3 | 11.1 |

As is evident from the results shown in Table 5, γ-CD is formed with a high yield when the substrate is used in a low concentration of 2%, but the yield of γ-CD decreases and the β-CD yield increases when the substrate concentration is increased or the reaction time is prolonged even at a substrate concentration of 2%.

TEST EXAMPLE 3

The solution of γ-CGTase obtained in Example 1 (5 units per 1 g of dry starch) was added to 10 ml of 5 to 10% soluble starch solution (0.01M McIlvaine buffer, pH 7.0), and the enzyme reaction was carried out for 22 hours at 40° C. In this case, ethyl alcohol (final concentration: 5 to 30% (v/v) based on the volume of the substrate solution) was added to the reaction system to examine its effect to enhance formation of each CD. Formation ratio of each CD (weight ratio to the substrate) by the Brevibacterium sp. γ-CGTase in the presence of ethyl alcohol is shown in Table 6.

TABLE 6

| Substrate | Ethyl Alcohol | CD Forming Ratio (%) | | | |
|---|---|---|---|---|---|
| (%) | (%) | α-CD | β-CD | γ-CD | T-CD |
| 5.0 | 0 | — | 12.0 | 6.8 | 18.7 |
| | 5.0 | — | 9.9 | 9.6 | 19.5 |
| | 10.0 | — | 7.3 | 12.4 | 19.7 |
| | 20.0 | — | 3.4 | 15.9 | 19.3 |
| | 25.0 | — | 0.9 | 8.9 | 9.8 |
| | 30.0 | — | 0.7 | 7.2 | 7.9 |
| | 0 | — | 8.5 | 4.6 | 13.1 |
| | 5.0 | — | 8.5 | 5.9 | 14.4 |
| 10.0 | 10.0 | — | 6.9 | 8.5 | 15.4 |
| | 20.0 | — | 2.5 | 11.6 | 14.1 |
| | 25.0 | — | 0.6 | 5.0 | 5.6 |
| | 30.0 | — | 0.5 | 4.8 | 5.3 |

As is evident from the results shown in Table 6, formation of γ-CD is enhanced and formation of β-CD is repressed when ethyl alcohol is added to a final concentration of 5 to 30% (v/v). Thus, addition of ethyl alcohol renders possible high yield formation of γ-CD with repressed formation of β-CD even in a high concentration substrate solution.

EXAMPLE 4

The solution of γ-CGTase obtained in Example 1 (5.0 units per 1 g of dry starch) was added to 10 ml of 10% soluble starch solution (0.01M McIlvaine buffer, pH 7.0) containing 20% (v/v) ethyl alcohol, and the enzyme reaction was carried out for 20 hours at 40° C. Yields of the γ-CD and β-CD formed by this reaction (weight ratio to the substrate) were found to be 16.5% and 3.5%, respectively, with no formation of α-CD.

Thus, it is apparent that there has been provided, in accordance with the present invention, a process for the production of a novel γ-CGTase which comprises culturing a strain belonging to the genus Brevibacterium capable of producing γ-CGTase, thereby allowing the strain to produce the novel γ-CGTase in a culture medium, and subsequently collecting the enzyme, as well as a process for the production of γ-CD in which the novel γ-CGTase is used.

Also, the present invention has succeeded in providing a process for the production of γ-CD in an industrial scale at a low cost without accompanying yield increment of T-CD by adding ethyl alcohol to a reaction solution in which γ-CD and β-CD are formed by the reaction of γ-CGTase with a high concentration of starch, thereby repressing formation of β-CD and enhancing formation of γ-CD.

Development of the process according to the present invention has rendered possible low cost production of γ-CD and therefore expands practical use of γ-CD to the field of food and feed.

While the invention has been described in detail and with reference to specific embodiments thereof, it will be apparent to one skilled in the art that various changes and modifications can be made therein without departing from the spirit and scope thereof.

What is claimed is:

1. A process for producing γ-cyclodextrin glucanotransferase which comprises:

(1) culturing Brevibacterium sp. FERM BP-4537 or a mutant thereof, in an aqueous nutrient culture medium containing assimilable sources of carbon, nitrogen and inorganic salts under conditions such that said Brevibacterium sp. FERM BP-4537 or said mutant thereof produces and secretes γ-cyclodextrin glucanotransferase into said culture medium, and (2) collecting the resulting culture medium of step (1) containing said cyclodextrin glucanotransferase, and (3) purifying said γ-cyclodextrin glucano-transferase from the collected culture medium of step (2), wherein when purified, the collected γ-cyclodextrin glucanotransferase has the following properties:

(a) action and substrate specificity: acts upon a substrate selected from the group consisting of starch, dextrin and maltooligosaccharides to produce γ-cyclodextrin as a primary product and β-cyclodextrin as a secondary product;

(b) optimum reaction pH: about 8 to about 9;

(c) optimum reaction temperature: around 45° C.;

(d) pH stability: about 6 to about 8; and (e) temperature stability: about 85% activity remains after 30 minutes at 40° C. in the absence of a calcium salt, and about 100% activity remains after 30 minutes at 45° C. in the presence of 20 mM of a calcium salt.

* * * * *